(12) United States Patent
Prien

(10) Patent No.: US 7,776,038 B2
(45) Date of Patent: Aug. 17, 2010

(54) INTRAMEDULLARY LOCKING NAIL

(75) Inventor: Ole Prien, Kiel (DE)

(73) Assignee: Stryker Trauma GmbH (DE)

( * ) Notice: Subject to any disclaimer, the term of this patent is extended or adjusted under 35 U.S.C. 154(b) by 601 days.

(21) Appl. No.: 11/224,559

(22) Filed: Sep. 12, 2005

(65) Prior Publication Data

US 2006/0064096 A1    Mar. 23, 2006

(30) Foreign Application Priority Data

Sep. 15, 2004    (DE) ............... 20 2004 014 288 U

(51) Int. Cl.
*A61B 17/58* (2006.01)
(52) U.S. Cl. .......................... 606/67; 606/62
(58) Field of Classification Search ............ 606/62–64, 606/61, 67, 69–71, 316; 248/222.41, 223.21; 411/418, 419
See application file for complete search history.

(56) References Cited

U.S. PATENT DOCUMENTS

| | | | | |
|---|---|---|---|---|
| 3,030,059 | A | * | 4/1962 | Jahn ................ 249/219.2 |
| 3,716,050 | A | * | 2/1973 | Johnston ............ 606/69 |
| 6,106,528 | A | * | 8/2000 | Durham et al. ........ 606/64 |
| 6,138,407 | A | * | 10/2000 | Pierce, Jr. ............ 47/46 |
| 6,309,159 | B1 | * | 10/2001 | Weaver et al. ........ 411/387.5 |
| 6,547,791 | B1 | | 4/2003 | Buhren et al. |
| 6,579,294 | B2 | | 6/2003 | Robioneck |
| 2003/0074000 | A1 | * | 4/2003 | Roth et al. ............ 606/62 |
| 2005/0015089 | A1 | * | 1/2005 | Young et al. .......... 606/69 |
| 2006/0095039 | A1 | * | 5/2006 | Mutchler ............. 606/64 |

FOREIGN PATENT DOCUMENTS

| | | |
|---|---|---|
| DE | 35 41 597 A1 | 6/1986 |
| DE | 35 37 318 A1 | 9/1986 |
| WO | WO-97/34539 A1 | 9/1997 |
| WO | WO-98/24380 A1 | 11/1998 |
| WO | WO-99/44528 A1 | 9/1999 |
| WO | WO-00/71040 B1 | 11/2000 |

* cited by examiner

*Primary Examiner*—Eduardo C Robert
*Assistant Examiner*—Elana B Fisher
(74) *Attorney, Agent, or Firm*—Lerner, David, Littenberg, Krumholz & Mentlik, LLP

(57) ABSTRACT

An intramedullary locking nail for treating bone fractures and which have spaced apart regions has at least one transverse hole for receiving a bone screw and at least one transverse hole being configured as an elongate hole extending in the longitudinal axial direction of the nail. An end portion of the elongate hole being wider than an adjacent portion of the elongate hole. The adjacent portion of the elongate hole having a constant width over its length. A bone screw is provided having a cross-sectional contour having a flattened segment. The end portion of the elongate hole being formed such that the bone screw is locked in a first rotational position in the end portion, and in a second rotational position, may enter the adjacent portion unhindered from the end portion.

11 Claims, 2 Drawing Sheets

INTRAMEDULLARY LOCKING NAIL

BACKGROUND OF THE INVENTION

The invention relates to an intramedullary locking nail for treating bone factures having spaced apart bone fragments. The nail has an elongated longitudinally extending slot adjacent one end.

Locking nails are known to be used for treating bone fractures of the long bones, i.e., in particular of the femur humerus and the tibia. At least one respective transverse hole is provided in the end regions of the locking nail, for receiving a bone screw. As a result, the fracture fragments are secured both in the torsional and the axial direction.

With locking nails, a distinction is made between static and dynamic locking. With static locking the bone screws are received in circular holes or bores of the nail. When the bone fragments grow together, shortening frequently results due to a sintering process. As there is a rigid connection between the locking nail and the bone, the bone fragments cannot yield. Thus there is the possible risk that the bone fragments will not grow together securely.

In order to prevent the described occurrence, so-called dynamic locking has become known. To this end, at least one transverse hole is configured as an elongate hole or slot, so that the bone screw can move with the bone fragment a certain distance relative to the nail. Dynamic locking is therefore also to be provided when a system for compression is associated with the locking nail. The bone fragments are pressed against one another with the aid of this system for compression after the locking nail has been introduced. Such nails are shown in U.S. Pat. Nos. 6,547,791 and 6,579,294.

SUMMARY OF THE INVENTION

One aspect of the invention is to provide an intramedullary locking nail for treating bone fractures with which static or dynamic locking can optionally be carried out.

These and other aspects of the invention are provided by an intramedullary locking nail for treating bone fractures which have spaced apart bone fracture regions. The intramedullary nail has at least one transverse bore for receiving a first bone screw and at least one transverse elongated bore for receiving a second bone screw. The elongated bore extends parallel or coaxially with the longitudinal axis of the bone nail. The elongate bore preferably has end portions separated by an adjacent central portion. The ends portions are preferably circular and have a diameter which is greater than the width of the central portion. The central portion preferably has a constant width over its entire length. A bone screw is provided having, in the preferred embodiment, a cross-sectional contour which is part-circular but with a flattened segment. The circular portion of the bone screw cross-section conforms to the diameter of the end portions of the elongated slot and can be received therein. However, the maximum diameter of the circular cross-section of the bone screw is greater than the width of the slot. However, the width of the bone screw perpendicular to the flattened section may be slidably received within the central portion of the elongate slot. Consequently, in one rotational position, the bone screw can be located in either of the end portions of the slot and can not slide, in that position, into the central region of the elongate slot portion. However, when rotated, preferably 90 degrees in either direction the flattened portion of the bone screw cross-section is then aligned with the central slot portion and may be slid out of either end portion and into the central portion of the slot.

In the preferred embodiment, the end portion of the slot has a circular periphery the mid-point of which is transversely offset relative to a longitudinal axis of the adjacent central portion of the slot. The offset is such that a longitudinal edge of the central portion forms a tangent to the circular periphery of the bore or slot end portion. In an alternate embodiment, the bone screw may include two diametrically opposite flat portions. The perpendicular spacing of which corresponds to the width of the adjacent central portion of the elongate slot or hole.

With the locking nail according to the invention, an end portion of the elongate hole or slot is wider than an adjacent portion of the elongate hole. A bone screw has a cross-sectional contour and the slot end portion has a contour which are formed such that the bone screw is locked in a first rotational position in the end portion and in a second rotational position may enter the adjacent portion unhindered from the end portion.

According to the invention, the cross-section of the bone screw to be used therefore has a contour deviating from the circular form and therefore different diameters or widths of the cross-section profile. In one orientation, the width is such that the bone screw can move into the portion adjacent to the end portion. A further width is, however, greater than the width of the adjacent central slot portion, so that the bone screw is locked in the end portion. The end portion therefore is wider transversely to the longitudinal extension of the elongate hole or slot than the portion of the elongate hole adjacent to the end portion.

The nail according to the invention allows the surgeon to choose between static or dynamic locking depending on the rotational position of the bone screw after being screwed into the bone and through the elongate hole. To this end, the bone screw can comprise a mark on the head, whereby the surgeon can identify whether dynamic or static locking has been set. Furthermore, it is also possible to convert initial static locking into dynamic locking, by the bone screw being rotated at a later time by a pre-determined angle, so that a relative movement between the bone screw and the nail is then possible. Finally, it is therefore conceivable to set static locking initially for compression purposes and after completing the compression to "switch" to dynamic locking.

Different cross-sectional contours of the bone screw and the end portion of the elongate hole are conceivable to produce the disclosed effect. A particularly simple embodiment of the invention provides that the end portion is defined by a circular edge, the mid point of which being offset transversely relative to the longitudinal axis of the adjacent portion, such that a longitudinal edge of the adjacent portion forms a tangent to the circle. In addition, the diameter of the circle is greater than the width of the adjacent portion. With this shape of hole, the cross-section of the bone screw only needs to have one flat portion, the width of the cross-section perpendicular to the flat portion being slightly smaller than the width of the adjacent portion. A bone screw with this contour can be relatively simply made and also effectively screwed into the bone.

In an alternative embodiment of the invention the end portion is also circular, its mid point, however, being located on the longitudinal axis of the adjacent portion of the elongate hole. In this case, the cross-section of the bone screw has two diametrically opposing flat portions, the perpendicular spacing of which corresponding to the width of the adjacent portion of the elongate hole. This shape can also be relatively simply produced but leads to a greater cross-sectional weakening of the bone screw than with a single flat portion.

BRIEF DESCRIPTION OF THE DRAWINGS

The invention is to be described in more detail hereinafter with reference to an embodiment shown in the drawing in which.

DETAILED DESCRIPTION

Figure 1:
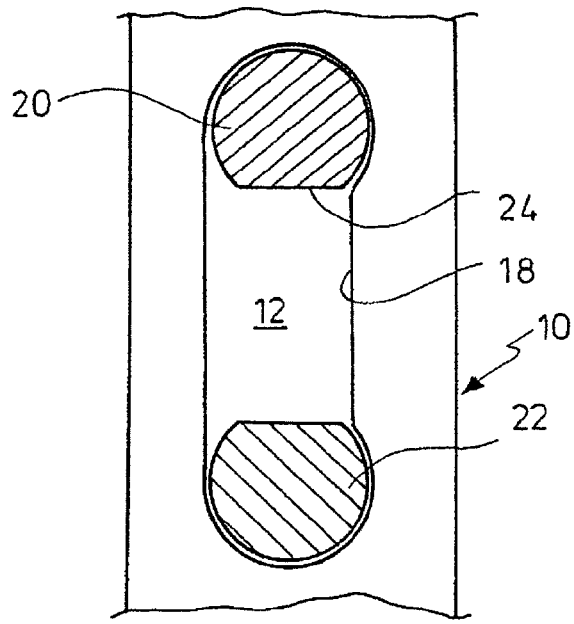
FIG. 1 is a portion of a locking nail with the features according to the invention.
Figure 2:
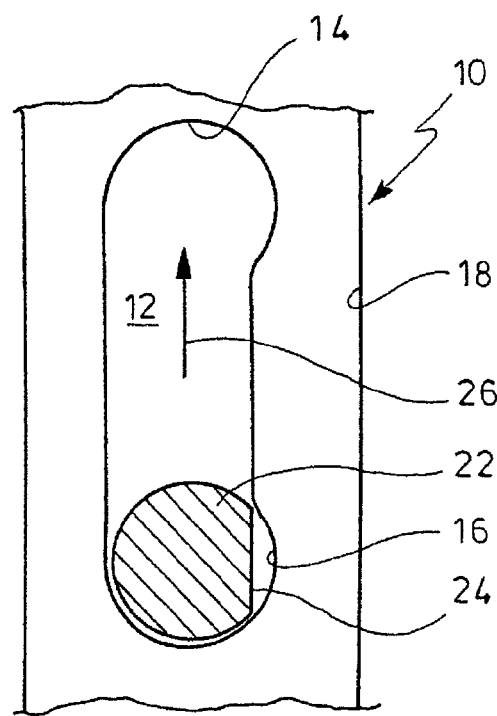
FIG. 2 is the same view as FIG. 1 but with dynamic locking.
Figure 3:
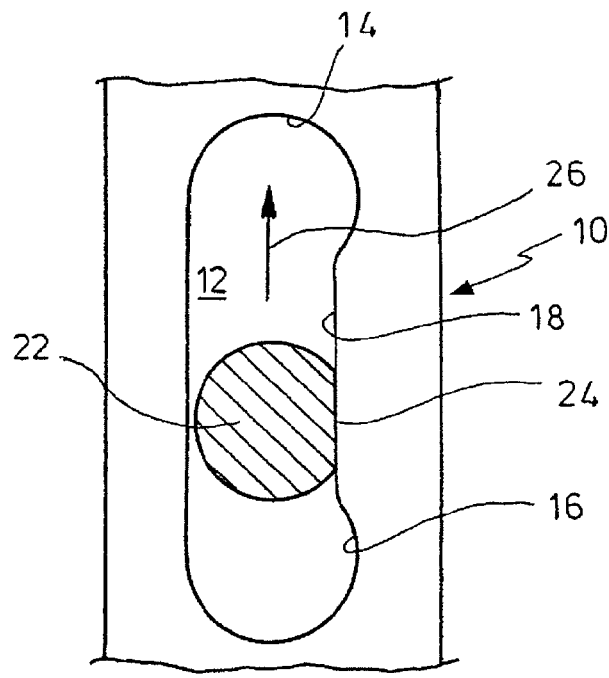
FIG. 3 is a similar view to FIG. 2 but with dynamic locking taking effect.
Figure 4:
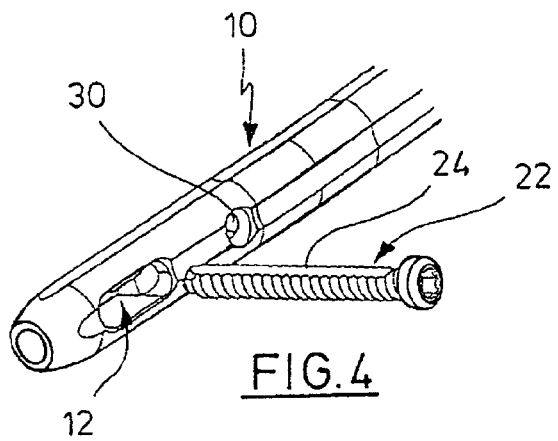
FIG. 4 is a perspective view of a locking nail with a bone screw according to the invention.

A locking nail 10 is shown in FIGS. 1 to 3, for example for a femur. The upper end is proximally oriented and the lower end is distally oriented, there being no difference whether the proximal end or the distal end of the locking nail is shown. It is known for at least one transverse hole or bore or a transverse hole or bore to be provided both at the distal and at the proximal end of a locking nail to receive a bone screw. Preferably, this is a circular hole or bore.

The locking nail 10 comprises an elongate hole 12 which is defined by a circular arc-shape contour at the ends, as is indicated by 14 and 16. A connecting portion is located between the end portions with edges 18 spaced parallel apart from one another. It can be seen from the FIGS. 1-3 that in the preferred embodiment the left edge forms a tangent to the circular edges 14, 16. The mid point of circular edges 14, 16 is located offset to the longitudinal axis of the connecting portion and the diameter of the circular edges 14, 16 is greater than the spacing of the edges 18 of the connecting portion. In FIG. 1 the cross-sectional profile of two bone screws 20, 22 is shown, which are respectively arranged in end portions 14 and 16 of the elongate hole 12. The diameter of the bone screws 20, 22 is slightly smaller than the diameter of the circular edges 14, 16. As can furthermore be seen, bone screws 20, 22 have a flat portion 24 in cross-section. In the rotational position of the bone screws 20, 22 shown in FIG. 1, bone screws 20, 22 are "locked" in the end portions. In other words, they cannot move out of end portions 14, 16 when a relative axial force is applied between the nail 10 and bone screws 20, 22.

Only one bone screw can be used and bone screw 20 is omitted from FIG. 2 and the bone screw 22 rotated about 90 degrees. It can be seen that the diameter of the bone screw 22 perpendicular to the flat portion 24 is slightly smaller than the spacing of the longitudinal edges 18. A relative movement can then take place between the elongate hole 12 and the bone screw 22, as is shown in FIG. 3. The direction of movement is indicated by arrow 26.

It is understood that the cross-sections of the bone screws 20, 22 shown in the Figures depict the shank cross-section and the head of the bone screw 20, 22 may be larger in diameter for the purpose of more effective location on the corticalis.

The locking nail 10 and bone screw 22 according to FIGS. 1 to 3 are shown in FIGS. 4 to 10 in perspective. The distal or proximal end of the locking nail is seen, depending on how it is inserted into the bone for treatment. The respective other end of the locking nail 10 is not shown. It may be of conventional design.

Figure 5:
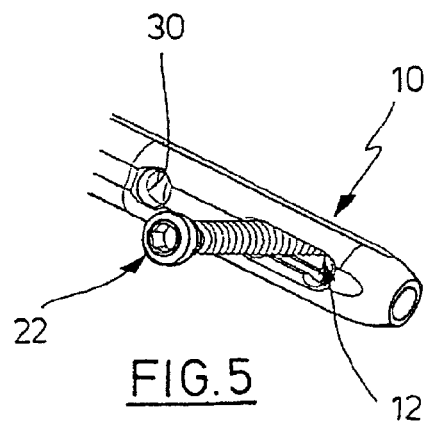
FIG. 5 is the view according to FIG. 4 with the bone screw inserted, comparable with the diagrammatic view according to FIG. 2.
Figure 6:
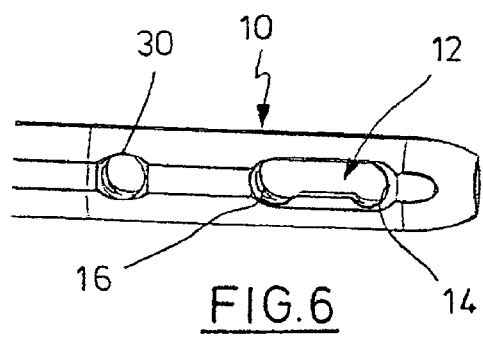
FIG. 6 is an enlarged side view of the locking nail according to FIG. 4.
Figure 7:
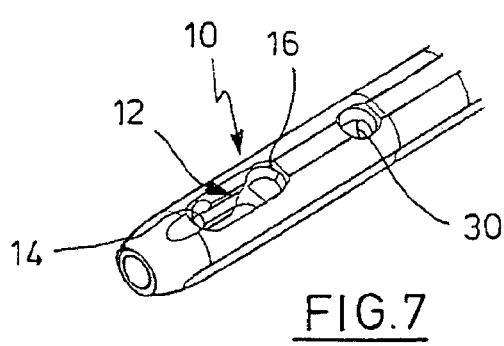
FIG. 7 is a further view of the locking nail according to FIG. 6.
Figure 8:
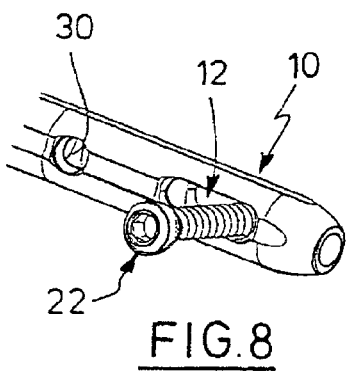
FIG. 8 is a similar view to FIG. 5 but in a further position of the bone screw.
Figure 9:
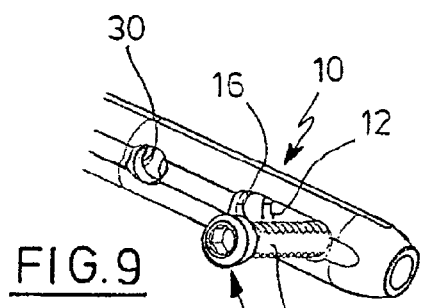
FIG. 9 is the same view as FIG. 8 but with the bone screw rotated.
Figure 10:
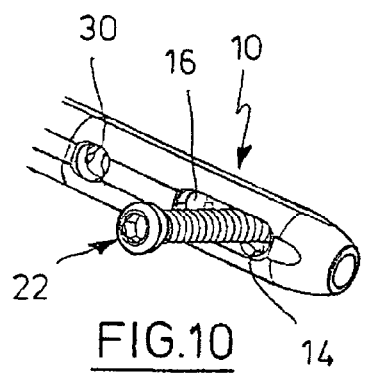
FIG. 10 is a similar view to FIGS. 8 and 9 but with a relative displacement between the locking nail and bone screw corresponding to FIG. 3.

Furthermore, it can be seen that in addition to the specially designed elongate hole 12 of the present invention which, as disclosed, extends transversely through the nail 10, a circular aperture 30 is provided through which a bone screw may also be passed. A bone screw does not however have to be provided with a flat portion 24, as the screws 20, 22. In FIG. 5, the bone screw 22 is positioned in the widened region 16 of the elongate hole 12 in FIGS. 8 and 9 in the widened region 14 of the elongate hole 12. In FIGS. 8 and 10 the flat portion 24 (not visible) is provided toward the bottom, so that, as shown in FIG. 10, a relative movement of the nail 10 and the bone screw 22 is possible. In FIG. 9, however, locking between the bone nail 10 and the bone screw 22 is shown, so that a relative movement between the parts is prevented.

In use, the surgeon inserts the intramedullary nail within the femur and places a first cross-locking bone screw through a bore at one end of the nail and then places a second bone screw through the elongated bore 12. The surgeon may either place the screw 22 in end portion 14 or 16 if he does not desire to have a dynamic fixation of the nail. As discussed above, in the preferred embodiment the head of the screw will have an indicator showing the orientation of the flattened portion. Should he wish to move the nail with respect to bone screw 22 he would then orient the screw such that the flattened portion 24 is parallel to the edge 18 of the elongated bore 12 which would then allow screw 22 to move axially with respect to the nail. Note the surgeon could orient the flat on either edge 18 of the elongated bore. However, should the surgeon decide to move the screw into either end portion 14 or 16, then the flat would be oriented on the edge 18 of elongated bore 12 opposite the tangential intersection between the central portion and the ends 14 or 16. Once rotated in the end portions 14 or 16, the screw 22 may be rotated 90 degrees which locks the screw in the axial direction with respect to the nail.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intramedullary locking nail system for treating bone fractures which have spaced apart regions comprising:

a nail having a shank with at least one hole for receiving a bone screw and at least one elongate hole elongated in an axial direction of the shank having two circular end portions, the circular end portions of the elongate hole being wider than an elongated adjacent hole portion of the elongate hole, the elongated adjacent hole portion having a length and a constant width over its length, wherein a longitudinal edge of the elongated adjacent hole portion forms a tangent to a circular periphery of the circular end portions; and a bone screw having a longitudinal extension and a cross-sectional contour deviating from a substantially circular form in a direction perpendicular to its longitudinal extension, wherein the bone screw is locked in one of the circular end portions in a first rotational position thereof and the bone screw may enter the elongate adjacent hole portion from the circular end portions in a second rotational position.

2. The locking nail system as set forth in claim 1 wherein the two circular end portions of the elongate hole are identically configured.

3. The locking nail system as set forth in claim 1 wherein the circular end portions are defined by a circular periphery, a mid point of which being located transversely offset relative to a longitudinal axis of the elongated adjacent hole portion; wherein the cross-sectional contour of the bone screw comprises a flat segment and a diameter of the cross-sectional contour of the bone screw perpendicular to the flat portion generally corresponding to the width of the elongated adjacent hole portion.

4. An intramedullary nail system comprising:
- a longitudinally extending shank portion having an elongate through bore, said elongate through bore having a first elongate portion having opposed edges defining a width of said first elongate portion, said opposed edges extending generally parallel to a longitudinal axis of said shank portion, said elongate through bore having part-circular second and third portions communicating respectively with a first and a second end of said first elongate portion, said part-circular second and third portions each having a diameter in a direction perpendicular to said longitudinal axis greater than said first elongate portion width; and
- a bone screw having a shank with a part-circular cross-section having a diameter across a circular portion of said cross-section greater than a width of the through bore first elongate portion and a flat formed on a side of said shank defining a cross-sectional width less than the width of said first elongate portion, the cross-section extending along a length of the bone screw thereby allowing the bone screw to be locked in a first rotational position thereof in the part-circular second and third portions and, in a second rotational position, the bone screw may enter the first elongate bore portion from either the second of third part-circular portions.

5. The intramedullary nail system as set forth in claim 4 wherein said third part-circular portion is identical to said second part-circular portion.

6. The intramedullary nail system as set forth in claim 4 wherein a center of said part-circular second portion diameter and a center of said part-circular third portion diameter is offset from a center of said first portion width.

7. The intramedullary nail system as set forth in claim 4 wherein said bone screw has a pair of diametrically opposed flanks.

8. The locking nail system as set forth in claim 4 wherein the circular end portions are defined by a circular periphery, a mid point of which being located transversely offset relative to a longitudinal axis of the elongated adjacent hole portion; wherein the cross-sectional contour of the bone screw comprises a flat segment and a diameter of the cross-sectional contour of the bone screw perpendicular to the flat portion generally corresponding to the width of the elongated adjacent hole portion.

9. An intramedullary locking nail system for treating bone fractures which have spaced apart regions, comprising:
- a bone nail having a shank portion with at least one hole for receiving a bone screw and an elongated hole elongated in a direction of a longitudinal axis of the bone nail, two end portions of the elongate hole having a first width and an adjacent slot portion intermediate the two end portions having a second width, the first width being greater than the second width, wherein the two end portions are of the elongate hole are defined by a circular periphery of each of the two end portions; and
- an axially extending bone screw, the bone screw having a part-circular circumferential portion along a length thereof, the part-circular portion terminating at end points extending along the bone screw length, the end points being connected to form a recessed surface with respect to a diameter of the part-circular circumferential portion, the diameter of the part-circular portion being less than the first width and greater than the second width and a width of the bone screw along the length at the recessed surface being less than the second width.

10. The locking nail system as set forth in claim 9 wherein a center of each part-circular periphery is offset relative to a central longitudinal axis of the adjacent slot portion, wherein a diameter of each part-circular periphery is equal to the first width and the recessed surface of the bone screw comprises a planar segment.

11. The locking nail as set forth in claim 9 wherein the recessed surface of the bone screw is planar.

* * * * *